United States Patent
Ascher et al.

(10) Patent No.: US 6,784,193 B1
(45) Date of Patent: Aug. 31, 2004

(54) MUTILIN DERIVATIVES AND THEIR USE AS ANTIBACTERIALS

(75) Inventors: Gerd Ascher, Kundl (AT); Heinz Berner, Vienna (AT); Johannes Hildebrandt, Oeynhausen (AT)

(73) Assignee: Sandoz GmbH, Kundl (AT)

( * ) Notice: Subject to any disclaimer, the term of this patent is extended or adjusted under 35 U.S.C. 154(b) by 77 days.

(21) Appl. No.: 10/048,438

(22) PCT Filed: Jul. 28, 2000

(86) PCT No.: PCT/EP00/07309
§ 371 (c)(1),
(2), (4) Date: Jan. 28, 2002

(87) PCT Pub. No.: WO01/09095
PCT Pub. Date: Feb. 8, 2001

(30) Foreign Application Priority Data

Jul. 30, 1999 (GB) .............................................. 9918037

(51) Int. Cl.$^7$ ...................... A61K 31/445; A61K 31/33; C07D 211/40; C07D 211/60; C07D 211/00

(52) U.S. Cl. ...................... 514/331; 514/330; 514/183; 540/1; 546/242; 546/245; 546/246; 546/1; 546/184

(58) Field of Search ................................. 514/330, 331, 514/183; 546/242, 245, 246, 1, 184; 540/1

(56) References Cited

U.S. PATENT DOCUMENTS

| 4,107,164 A | 8/1978 | Egger et al. ................. 544/380 |
| 4,675,330 A | 6/1987 | Berner et al. ............... 514/365 |

FOREIGN PATENT DOCUMENTS

| DE | 22 48 237 | 4/1973 |
| EP | 013 768 | 6/1980 |
| EP | 0 421 364 A2 | 4/1991 |
| WO | WO 99/21855 | 5/1999 |

*Primary Examiner*—Shengjun Wang
(74) *Attorney, Agent, or Firm*—Diane E. Furman; John D. Thallemer

(57) ABSTRACT

A compound of formula (I) wherein $R_2$ is arylene or heterocyclene; or R and $R_2$ together with the nitrogen atom to which they are attached form non-aromatic heterocyclene; and the other residues have various meanings, useful as pharmaceuticals, e.g. antimicrobials.

8 Claims, No Drawings

MUTILIN DERIVATIVES AND THEIR USE AS ANTIBACTERIALS

This application is a 371 of PCT/EP 00/07309, filed Jul. 8, 2000. Which claims the priority of UK 99/8037.04, filed Jul. 3, 1999.

The present invention relates to compounds having e.g. antimicrobial, e.g. antibacterial, activity; more specifically the present invention relates to mutilins.

In one aspect the present invention provides a compound of formula

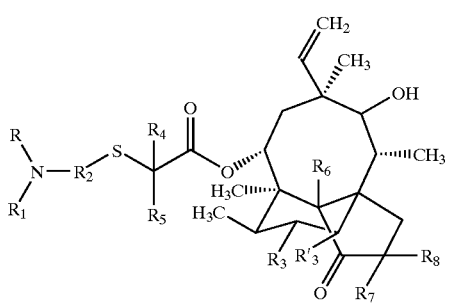

I wherein
R is hydrogen or alkyl;
$R_1$ is hydrogen or a group of formula

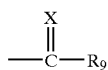

wherein
X is sulphur, oxygen, $NR_{10}$, wherein $R_{10}$ is hydrogen or alkyl, or $N^+(R'_{10})_2$ wherein $R'_{10}$ is alkyl in the presence of an appropriate anion;
$R_9$ is amino, alkyl, aryl, heterocyclyl or mercapto; and, if X is oxygen, $R_9$ is additionally hydrogen;
$R_2$ is arylene or heterocyclene;
$R_4$ is hydrogen or alkyl;
$R_5$ is hydrogen or alkyl;
$R_3$ and $R_3'$ are hydrogen or deuterium,
$R_6$, $R_7$ and $R_8$ are hydrogen or deuterium; or
R and $R_2$ together with the nitrogen atom to which they are attached form non-aromatic heterocyclene and $R_1$ is a group of formula

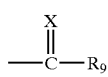

wherein X and $R_9$ are as defined above.

R is hydrogen or alkyl, e.g. ($C_{1-4}$)alkyl; preferably hydrogen.

$R_1$ is hydrogen or a group of formula —C(=X)$R_9$, e.g. a group of formula —C(=X)$R_9$.

X is sulphur, oxygen, $NR_{10}$, wherein $R_{10}$ is hydrogen or alkyl, e.g. ($C_{1-4}$)alkyl, or $N^+(R'_{10})_2$ wherein $R'_{10}$ is alkyl, e.g. ($C_{1-4}$)alkyl, in the presence of an appropriate anion; preferably oxygen.

$R_9$ is amino, alkyl, alkoxy, e.g. ($C_{1-4}$)alkoxy; aryl, heterocyclyl or mercapto; e.g. a group of formula —S—$R_{12}$, wherein $R_{12}$ is alkyl, e.g. ($C_{1-4}$)alkyl; and, if X is oxygen, $R_9$ is hydrogen, amino, alkyl, alkoxy, aryl, heterocyclyl or mercapto.

$R_9$ is preferably alkyl, e.g. ($C_{1-8}$)alkyl, such as ($C_{1-4}$) alkyl, e.g. unsubstituted or substituted alkyl, e.g. substituted by groups which are conventional in pleuromutilin chemistry, e.g. one or more amino, halogen, such as fluoro, e.g. trifluoroalkyl, such as trifluoromethyl; guanidinyl, hydroxy, heterocyclyl, e.g. including a 5 or 6 membered ring containing 1 or 2 nitrogen atoms; e.g. imidazolyl. If $R_9$ is alkyl substituted by amino, $R_9$ is preferably the residue of an amino acid, e.g. including valine, histidine, arginine, pipecolinic acid, e.g. said residue includes that part of an amino acid which remains if the carboxylic group is split off.

Or $R_9$ is preferably heterocyclyl, e.g. 5 or 6 membered heterocyclyl, e.g. containing one or two heteroatoms; e.g. selected from nitrogen; e.g. condensed with a further ring (system), e.g. the further ring system including phenyl; preferably piperidinyl, pyrrolidinyl, pyrrolyl, pyridinyl, benzimidazolyl, quinolinyl, triazolyl; e.g. unsubstituted heterocyclyl or substituted heterocyclyl, e.g. substituted by one or more alkyl, e.g. methyl; hydroxy, amino, nitro, a group $COOR_{13}$, wherein $R_{13}$ is alkyl, e.g ($C_{1-4}$)alkyl, such as tert.butyl; e.g. preferably substituted by one or more alkyl hydroxy, amino, nitro.

If $R_9$ is heterocyclyl, e.g. piperidinyl, hydrogen atoms of the heterocyclyl ring, e.g. in piperidinyl; the hydrogen atom attached to the nitrogen atom of the ring system may be replaced by deuterium.

Amino in the meaning of $R_9$ includes a free amine group, alkyl- and dialkylamine and amine substituted by —$COOR_{11}$, wherein $R_{11}$ is alkyl, preferably ($C_{1-4}$)alkyl.

$R_2$ is arylene, such as phenylene, e.g. unsubstituted arylene or substituted arylene, e.g. substituted by groups which are conventional in pleuromutilin chemistry; e.g. one or more hydroxy, alkyl, e.g. ($C_{1-4}$)alkyl; halogen, e.g. fluoro; trifluoroalkyl; nitro; or heterocyclene. Heterocyclene as used herein is a heterocyclic ring, wherein two bonds are the bonds to the vicinal nitrogen and sulphur group in a compound of formula I. Preferably $R_2$ is arylene, e.g. unsubstituted arylene or arylene substituted by one or more groups which are conventional in pleuromutilin chemistry, e.g. alkyl, e.g. ($C_{1-4}$)alkyl, such as methyl; halogen such as fluoro; trifluoroalkyl, such as trifluoromethyl. Arylene and heterocyclene in the meaning of $R_2$ are bound to a sulphur atom and to —N(R)($R_1$) in a compound of formula I. These two bonds may be vicinal or in another position, e.g. in ortho, para or meta position; in the corresponding ring system. Heterocyclene is preferably bound to the sulphur atom and to —N(R)($R_1$) in a compound of formula I via carbon atoms of heterocyclene.

$R_4$ is hydrogen or alkyl; preferably hydrogen or ($C_{1-4}$) alkyl, e.g. methyl.

$R_5$ is hydrogen or alkyl, preferably hydrogen or ($C_{1-4}$) alkyl such as methyl; e.g. unsubstituted alkyl or substituted alkyl, e.g. substituted by hydroxy; more preferably $R_5$ is hydrogen.

$R_3$ and $R'_3$ are hydrogen or deuterium, preferably hydrogen. $R_6$, $R_7$ and $R_8$ are hydrogen or deuterium.

If $R_1$ is a group of formula —C(=X)—$R_9$, R and $R_2$ together with the nitrogen atom to which they are attached may form non-aromatic heterocyclene, e.g. having 5 to 6 ring members and one heteroatom, e.g. nitrogen; preferably including piperidinyl, pyrrolidinyl, preferably piperidine. Preferably said heterocyclene is bound to the sulphur group and to the —N($R_1$) group in a compound of formula I via heterocyclene carbon atoms.

If not otherwise defined herein heterocyclyl or heterocyclene includes a 5 or 6 membered ring having 1 to 4 heteroatoms selected from S, O and N; e.g. N; optionally condensed with a further ring (system), e.g. condensed with a phenyl ring; e.g. or condensed with a heterocyclyl ring, e.g. including quinoline, purine. Heterocycl(ene) includes unsubstituted or substituted heterocycl(ene), e.g. substituted by groups which are conventional in pleuromutilin chemistry, e.g. including alkyl; hydroxy, amino, nitro, a group COOR$_{13}$, wherein R$_{13}$ is alkyl. Alkyl includes (C$_{1-8}$)alkyl, e.g. (C$_{1-4}$)alkyl. Aryl includes phenyl.

In another aspect the present invention provides a compound of formula I, wherein R is hydrogen;
R$_1$ is hydrogen or a group of formula

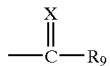

wherein X is sulphur, oxygen, NR$_{10}$, wherein R$_{10}$ is hydrogen or alkyl, or N$^+$(R'$_{10}$)$_2$ wherein
R'$_{10}$ is alkyl in the presence of an appropriate anion; e.g. Cl$^-$;
R$_9$ is amino, alkyl, heterocyclyl or mercapto; and, if X is oxygen, R$_9$ is additionally hydrogen;
R$_2$ is phenylene;
R$_4$ is hydrogen or alkyl;
R$_5$ is hydrogen;
R$_3$ and R$_3$' are hydrogen;
R$_6$, R$_7$ and R$_8$ are hydrogen or deuterium; or
R and R$_2$ together with the nitrogen atom to which they are attached form non-aromatic heterocyclene and R$_1$ is a group of formula

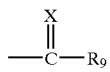

wherein X is oxygen and R$_9$ is alkyl.

In another aspect the present invention provides a compound of formula

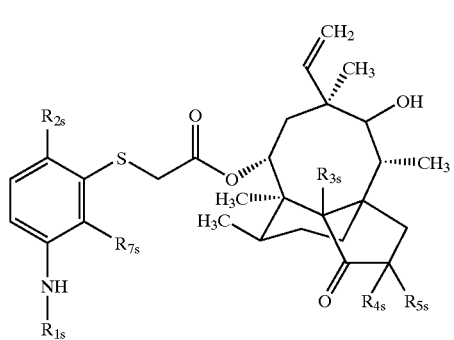

Is wherein R$_{1s}$ is hydrogen or a group of formula

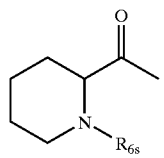

e.g. a group of formula

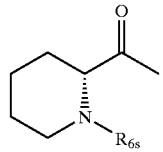

wherein R$_{6s}$ is hydrogen or deuterium;
R$_{2s}$ is hydrogen, methyl or tert-butyl;
R$_{7s}$ is hydrogen or methyl; and
R$_{3s}$, R$_{4s}$ and R$_{5s}$ are hydrogen or deuterium; and a compound of formula

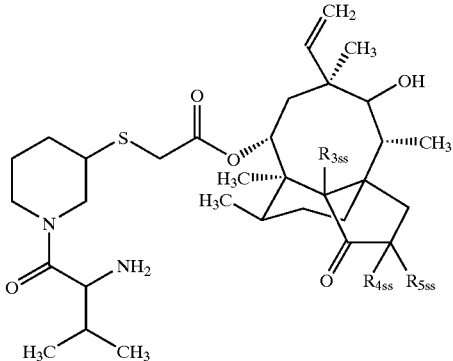

Iss wherein R$_{3ss}$, R$_{4ss}$ and R$_{5ss}$ are hydrogen or deuterium.

A compound of formula I includes a compound of formulae Is and Iss.

In another aspect the present invention provides a compound of formula I, e.g. including a compound of formula Is and Iss in the form of a salt, or in the form of a salt and in the form of a solvate, or in the form of a solvate.

In another aspect the present invention provides

14-O-(3-amino)phenyl-sulfanylacetyl)-mutilin, e.g. in free form or in the form of a salt, e.g. with hydrochloric acid;

14-O-(3-amino)phenyl-sulfanylacetyl)-2,2,4-trideuteromutilin, e.g. in free form or in the form of a salt, e.g. with hydrochloric acid or with deuterochloric acid;

14-O-(3-(piperidin-2-yl-carbonylamino)-phenyl-sulfanylacetyl)mutilin, e.g. in free form or in the form of a salt, e.g. with hydrochloric acid;

14-O-(3-(piperidin-2-yl-carbonylamino)phenyl-sulfanylacetyl) -2,2,4-trideutero-mutilin, e.g. in free form or in the form of a salt, e.g. with hydrochloric acid or deuterochloric acid;

14-O-(3-(piperidin-2-yl-carbonylamino)-2,5-dimethyl-phenylthio-methylcarbonyl)mutilin, e.g. in free form or in the form of a salt, e.g. with hydrochloric acid;

14-O-(3-(piperidin-2-yl-carbonylamino)-2,5-dimethyl-phenylthio-methylcarbonyl)-2,2,4-trideutero-mutilin, e.g. in free form or in the form of a salt, e.g. with hydrochloric acid or with deuterochloric acid;

14-O-(3-(piperidin-2-yl-carbonylamino)-5-tert.butyl-phenyl-sulfanylacetyl)mutilin, e.g. in free form or in the form of a salt, e.g. with hydrochloric acid;

14-O-(3-(piperidin-2-yl-carbonylamino)-5-tert.butyl-phenyl-sulfanylacetyl)-2,2,4-trideutero-mutilin, e.g. in free form or in the form of a salt, e.g. with hydrochloric acid or with deuterochloric acid;

14-O-(1(2-amino-isobutylcarbonyl)-piperidin-3-yl-sulfanylacetyl)mutilin, e.g. in free form or in the form of a salt, e.g. with hydrochloric acid; and 14-O-(1(2-amino-isobutylcarbonyl)-piperidin-3-yl-sulfanylacetyl)-2,2,4-trideutero-mutilin, e.g. in free form or in the form of a salt, e.g. with hydrochloric acid or with deuterochloric acid.

A salt of a compound of formula I includes a pharmaceutically acceptable salt, e.g. including a metal salt or an acid addition salt. Metal salts include for example alkali or earth alkali salts; acid addition salts include salts of a compound of formula I with an acid, e.g. hydrogen fumaric acid, fumaric acid, naphthalin-1,5-sulphonic acid, hydrochloric acid, deuterochloric acid; preferably hydrochloric acid or deuterochloric acid.

A compound of formula I in free form may be converted into a corresponding compound in the form of a salt; and vice versa. A compound of formula I in free form or in the form of a salt and in the form of a solvate may be converted into a corresponding compound in free form or in the form of a salt in unsolvated form; and vice versa.

In another aspect the present invention provides a compound of formula

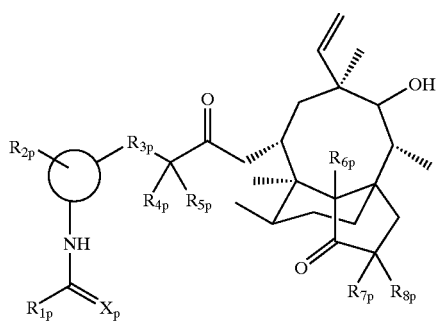

Ip wherein
$R_{1p}$ is hydrogen, amino, alkyl, aminoalkyl or an optionally amino and/or hydroxy- and/or nitrosubstituted 5- or 6-membered heteroaromatic or heteroalicyclic ring with 1 to 3 nitrogen atoms;

$R_{2p}$ represents an optionally alkyl-, fluoro- or trifluoromethylsubstituted aromatic, 5- or 6-membered heteroaromatic with 1 to 3 nitrogen atoms, purine or quinoline;

$R_{3p}$ represents S or O; preferably S;

$R_{4p}$ represents hydrogen or methyl;

$R_{5p}$ represents hydrogen, methyl or $CH_2OH$, $X_p$ represents NH or O; and $R_{6p}$, $R_{7p}$ and $R_{8p}$ are the same or different and represent hydrogen or deuterium, in free form or in form of an acid addition or quaternary salt.

A compound of formula I, including a compound of formulae Is, Iss and Ip, may exist in the form of isomers and mixtures thereof; e.g a compound of formula I may contain asymmetric carbon atoms and may thus exist in the form of diastereoisomeres and mixtures thereof. Isomeric or diastereoisomeric mixtures may be separated as appropriate, e.g. according to a method as conventional, to obtain pure isomers or diastereoismeres, respectively. The present invention includes a compound of formula I in any isomeric and diasteroisomeric form and in any isomeric and diastereoisomeric mixture.

Preferably the cofiguration in the mutilin ring of a compound of formula I is the same as in a naturally produced mutilin.

In another aspect the present invention provides a process for the production of a compound of formula I as defined above comprising the steps Either, a1. reacting a compound of formula

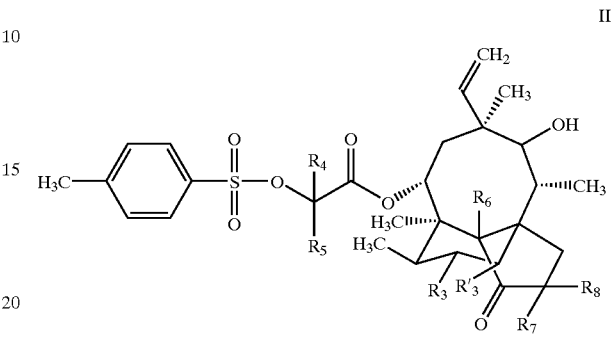

II wherein $R_3$, $R'_3$, $R_4$ and $R_5$ are as defined in formula I and $R_6$, $R_7$ and $R_8$ are hydrogen, with a compound of formula $N(R)(R_1)$—$R_2$—SH, wherein R, $R_1$ and $R_2$ are as defined in formula I, to obtain a compound of formula I, wherein R, $R_1$, $R_2$, $R_3$, $R'_3$, $R_4$ and $R_5$ are as defined in formula I and $R_6$, $R_7$ and $R_8$ are hydrogen;

and, if desired, b1. introducing deuterium into a compound of formula I obtained in step a1. to obtain a compound of formula I, wherein $R_6$, $R_7$ and $R_8$ are deuterium, and R, $R_1$, $R_2$, $R_3$, $R'_3$, $R_4$ and $R_5$ are as defined in formula I;

or a2. reacting of a compound of formula II as defined in step a1. with thiourea and subsequent reduction to obtain a compound of formula

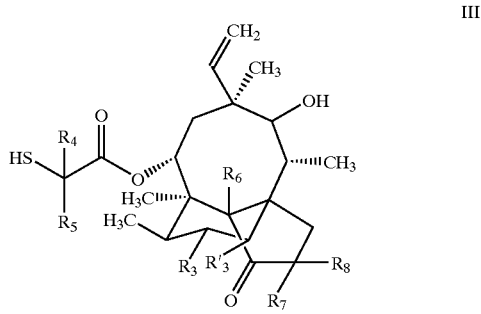

III wherein $R_3$, $R'_3$, $R_4$ and $R_5$ are as defined in formula I and $R_6$, $R_7$ and $R_8$ are hydrogen, b2. reacting a compound of formula III as defined in step a2. with a compound of formula $R_2(NO_2)_2$, wherein $R_2$ is as defined in formula I; or with a non-aromatic heterocyclic ring which carries a group of formula —C(=X)$R_9$ wherein X and $R_9$ are as defined in claim 1, in the form of a reactive derivative, e.g. a mesylate or a tosylate; to obtain a compound of formula

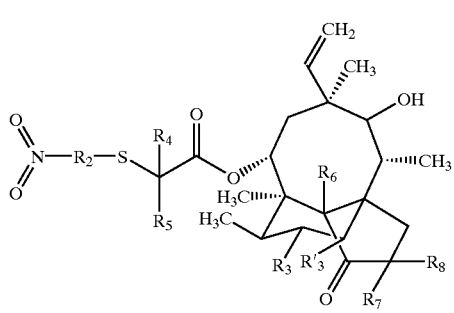
IV wherein $R_2$, $R_3$, $R'_3$, $R_4$ and $R_5$ are as defined in formula I and $R_6$, $R_7$ and $R_8$ are hydrogen, c2. reducing the nitro group in a compound of formula IV as defined in step b2., to obtain a compound of formula I, wherein $R_2$, $R_3$, $R'_3$, $R_4$ and $R_5$ are as defined in formula I and R, $R_1$, $R_6$, $R_7$ and $R_8$ are hydrogen; and, if desired, d2. reacting the amino group in a compound of formula I, as defined in step c2., to obtain a compound of formula I, wherein $R_1$ is a group of formula

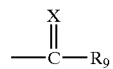

wherein R, $R_2$, $R_3$, $R'_3$, $R_4$, $R_5$, $R_9$ and X are as defined in formula I and $R_6$, $R_7$ and $R_8$ are hydrogen; and, if desired, e2. introducing deuterium into a compound of formula I as defined in step d2., to obtain a compound of formula I, wherein R, $R_1$, $R_2$, $R_3$, $R'_3$, $R_4$, $R_5$, $R_9$ and X are as defined in formula I and $R_6$, $R_7$ and $R_8$ are deuterium;

or a3. reacting a compound of formula

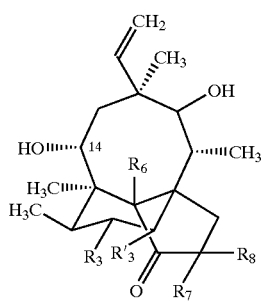
V wherein $R_6$, $R_7$ and $R_8$ are hydrogen and $R_3$ and $R'_3$ are hydrogen or deuterium, with a compound of formula

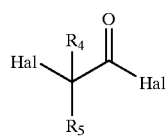

wherein $R_4$ and $R_5$ are as defined in formula I and Hal is halogen, e.g. chloro, bromo, iodo; to obtain a compound of formula

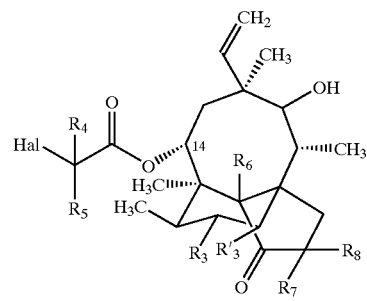
VI wherein $R_4$, $R_5$, Hal, $R_6$, $R_7$, $R_8$, $R_3$ and $R'_3$ are as defined in step a3.;

b3. reacting a compound of formula VI as defined in step a3. with a compound of formula HS—$R_2(NO_2)_2$, wherein $R_2$ is as defined in formula I, to obtain a compound of formula IV as defined in step b2., and further reacting a compound of formula IV according to step c2., and if desired, according to any one of steps d2. and e2. as defined above, to obtain a compound of formula I as defined in formula I.

Any compound of formula I, e.g. including a compound of formulae Is, Iss or Ip; may be prepared as appropriate, e.g. according to a method as conventional, e.g. or as specified herein. Any compound of formulae Is, Iss and Ip may be prepared, e.g. analogously, according to a process for the preparation of a compound of formula I.

A compound of formula II and of formula V is known or may be obtained according to a method as conventional.

Replacement of hydrogen atoms in a compound of formula I, e.g. in the form of a salt; by deuterium atoms may be carried out as appropriate, e.g. according to a method as conventional, e.g. or according to a method described herein; e.g. by treatment of a compound of formula I, e.g. including a compound of formula Is, Iss and Ip; with deuterochloric acid (DCl) in an appropriate solvent (system) and isolation of a compound of formula I, e.g. in the form of a salt, wherein hydrogen atoms, e.g. in the meaning of $R_6$, $R_7$ and $R_8$ are replaced by deuterium atoms.

The production of a compound of formula I, wherein $R_3$ and $R'_3$ is deuterium may be carried out as appropriate, e.g. according to a method as conventional, e.g. via treatment of a compound of formula V wherein the carbon atoms carrying $R_3$ and $R'_3$, which both are hydrogen, together form a double bond and which is a known compound, with deuterium to obtain a compound of formula V, wherein $R_3$ and $R'_3$ are deuterium; and further reacting a compound of formula V, wherein $R_3$ and $R'_3$ are deuterium as appropriate, e.g. according to a method as conventional, e.g. according to steps a3. to b3. as described above, to obtain a compound of formula I.

The compounds of formula I, e.g. including a compound of formulae Is, Iss and Ip, hereinafter designated as "active compound(s) of the present invention" exhibit pharmacological activity and are therefore useful as pharmaceuticals.

For example, the active compounds of the present invention show antimicrobial, e.g antibacterial, activity against gram negative bacterias, such as *Escherichia coli*; and against gram positive bacteria, such as *Staphylococcus aureus, Streptococcus pyogenes, Streptococcus pneumoniae*, Mycoplasms, Chalmydia and obligatory anaerobes, e.g. *Bacteroides fragilis*; in vitro in the Agar Dilution Test or Microdilution Test according to National Commftee for Clinical Laboratory Standards (NCCLS) 1997, Document M7-A4 Vol.17, No. 2: "Methods for dilution Antimicrobial Susceptibility Tests for Bacteria that Grow Aerobically—Fourth Edition, Approved Standard"; and e.g. in vivo in systemic infections in mice.

The active compounds of the present invention show antibacterial activitiy in vitro (MIC ($\mu$g/ml)) in the Agar Dilution Test or in the Microdilution Test from about $\leq 0.01$ $\mu$g/ml to 25 $\mu$g/ml, e.g. against above mentioned bacterial species; and are active against Mycoplasms and Chlamydia. MIC=minimal inhibitory concentration.

The active compounds of the present invention show activity in systemic infections of mice, e.g. against *Staphylococcus aureus* (e.g. strain ATCC 49951), e.g. when administered parenteral or oral, e.g. at dosages from about 8 to 150 mg/kg body weight; E.g. the $ED_{50}$ values for the compound of example 23 is 7.55 mg/kg body weight after subcutaneous administration; and 7.72 mg/kg body weight after oral administration. $ED_{50}$=Effective dosage in mg/kg body weight per application by which 50% of the treated animals are protected from death; calculated by Probit analysis (n=8 animals/group). It has, for example, been determined that the MIC 90% ($\mu$g/ml) of the compounds of examples 1 and 52 against, for example *Staphylococcus aureus*, e.g. strains ATCC 10390, ATCC 29213, ATCC 29506, ATCC 49951 or ATCC 9144, is of ca. $\leq 0.0125$ $\mu$g/ml; whereas for example the MIC 90% ($\mu$g/ml) of erythromycin A, as commercially available, is of ca. 0.2 to 0.4.

The active compounds of the invention show an surprising overall activity spectrum. For example, it has been determined that the active compounds of the present invention show surprising activity in vitro against *Enterococcus faecium*, including vancomycin-resistant strains; against *Staphylococcus aureus* including methicillin sensitive (MSSA) and methicillin-resistant (MRSA) strains; and against *Streptococcus pneumoniae* including penicillin-resistant strains; e.g. in the Agar Dilution Test or in the Micro Dilution Test in Mueller-Hinton agar or Mueller-Hinton broth with or without supplements according to the approved standard reference methods of the National Committee for Clinical Laboratory Standards (NCCLS), Document M7-A4 for aerobic bacteria.

For example it has been determined that the MIC ($\mu$g/ml) the compounds of examples 1 and 52 (both tested in the form of a hydrochloride) against for example *Staphylococcus aureus* MSSA is of ca. 0.025; whereas the MIC ($\mu$/ml) of azithromycin as commercially available is of ca. 1.6; that the MIC ($\mu$g/ml) of the compound of example 1 against for example *Staphylococcus aureus* MRSA is of ca. $\leq 0.0125$; whereas the MIC ($\mu$g/ml) of azithromycin as commercially available is of ca. >25.6; that the MIC ($\mu$g/ml) of the compounds of examples 1 and 52 against for example penicillin-resistant *Streptococcus pneumoniae* is of ca. $\leq 0.0125$; whereas the MIC ($\mu$g/ml) of azithromycin as commercially available is of ca. >2.56; and that the MIC of the compounds of examples 1 and 52 against for example vancomycin-resistant *Enterococcus faecium* is of ca. $\leq 0.0125$ to 0.025.

In another aspect the present invention provides a compound of formula I for use as a pharmaceutical, preferably as an antimicrobial, such as an antibiotic, e.g. and an anti-anaerobic.

In a further aspect the present invention provides a compound of formula I for use in the preparation of a medicament for the treatment of microbial diseases, for example of diseases caused by bacteria, e.g. selected from *Staphylococcus aureus, Streptococcus pyogenes, Streptococcus pneumoniae*, Mycoplasms, Chalmydia e.g. and obligatory anaerobes; e.g. including penicillin or multidrug-resistant strains, e.g. of *Streprococcus pneumoniae*; e.g. including vancomycin-resistant strains, e.g. of *Enterococcus faecium*; e.g. and including methicillin-resistant strains, e.g. of *Staphylococcus aureus*.

In a further aspect the present invention provides a method of treatment of microbial diseases which comprises administering to a subject in need of such treatment an effective amount of a compound of formula I; e.g. in the form of a pharmaceutical composition.

For antimicrobial treatment, the appropriate dosage will, of course, vary depending upon, for example, the active compound of the present invention employed, the host, the mode of administration and the nature and severity of the conditions being treated. However, in general, for satisfactory results in larger mammals, for example humans, an indicated daily dosage is in the range from about 0.5 to 3 g, of an active compound of the present invention conveniently administered, for example, in divided doses up to four times a day. An active compound of the present invention may be administered by any conventional route, for example orally, e.g. in form of tablets or capsules, or parenterally, e.g. in the form of injectable solutions or suspensions, e.g. in analogous manner to Erythromycins, e.g. azithromycin.

The compounds of examples 1, 12, 21, 23, 35 and 52 are preferred compounds of the present invention for use as an antimicrobial agent.

It has, for example been determined that the MIC ($\mu$g/ml) of the compounds of examples 1 and 52 (both tested in the form of an hydrochlorid) against, for example *Enterococcus faecalis* strain ATCC 29212 is ca. 0.8 to 6.4; whereas, for example ethromycin A, as commeraially available, shows an MIC ($\mu$/ml) of ca. 1.6. It is therefore indicated that for the treatment of microbial diseases, bacterial diseases the preferred compounds of the invention may be administered to larger mammals, for example humans, by similar modes of administration at similar dosages than conventionally employed with erythromycins, e.g. erythromycin A or azithromycin.

The active compounds of the present invention may be administered in the form of a pharmaceutically acceptable salt, e.g. an acid addition salt or metal salt; or in free form; optionally in the form of a solvate. The active compounds of the present invention in the form of a salt exhibit the same order of activity as the active compounds of the present invention in free form.

The present invention also provides a pharmaceutical composition comprising a compound of formula I in free form or in the form of a pharmaceutically acceptable salt; e.g. and/or in the form of a solvate; in association with at least one pharmaceutical carrier or diluent.

Such compositions may be manufactured according to a method as conventional. Unit dosage form may contain, for example, about 100 mg to about 1 g.

The active compounds of the present invention are additionally suitable as veterinary agents, e.g. veterinary active compounds, e.g. in the prophylaxis and in the treatment of microbial, e.g. bacterial diseases, in animals, such as fowl, pigs and calves; e.g. and for diluting fluids for artificial insemination and for egg-dipping techniques.

In another aspect the present invention provides a compound of formula I for use as a veterinary agent.

In a further aspect the present invention provides a compound of formula I for the preparation of a veterinary composition which is useful as a veterinary agent.

The present invention further provides a veterinary method for the prophylaxis and in the treatment of microbial, e.g. bacterial diseases which comprises administering to a subject in need of such treatment an effective amount of a compound of formula I, e.g. in the form of a veterinary composition.

For use of the active compounds of the present invention as a veterinary agent, the dosage will of course vary depending upon the size and age of the animal and the effect desired; for example for prophylactic treatment relatively low doses would be administered over a longer time period, e.g. 1 to 3 weeks. Preferred doses in drinking water are from 0.0125 to 0.05 weight by volume, particularly 0.0125 to 0.025; and in foodstuffs from 20 to 400 g/metric ton, preferably 20 to 200 g/metric ton. It is preferred to administer the active compounds of the present invention as a veterinary agent to hens in drinking water, to pigs in foodstuff and to calves orally or parenterally, e.g. in the form of oral or paraenteral preparations.

In the following examples which illustrate the invention references to temperature are in degrees Celsius.

The following abbreviations are used:

| | |
|---|---|
| DCCI | dicyclohexylcarbodilmide |
| DIEA | diisopropyl ethyl amine |
| BOC: | tert.butoxycarbonyl |
| PyBOP | (benzotriazol-1-yloxy) tripyrrolidinophosphonium-hexafluorophosphate |
| HMPT | hexamethylphosphorous triamide |
| DCl: | deuterochloric acid |

The numbering of the mutilin cyclus referred to in the examples is given in the following formula:

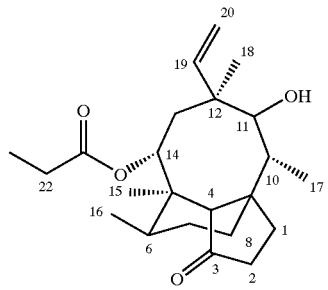

EXAMPLE 1

14-O-[(3-(Piperidine-2(R)-carbonyl)amino) phenylsulfanyl)acetyl]mutilin in the Form of a Hydrochloride 206 mg of DCCl are added to a solution of 229 mg of N—BOC—(R)-pipecolic acid and 485 mg of 14-O-[(3-amino-phenylsulfanyl)acetyl]mutilin in 20 ml of dichloromethane at room temperature and the mixture obtained is stirred for ca. 12 hours at room temperature. Urea precipitates, is filtrated off and the filtrate obtained is concentrated under reduced pressure. The concentrate obtained is subjected to chromatography (silica gel; cyclohexane/ethyl acetate=1/1). 14-O-[(3-(N—BOC—(R)-piperidine-2 (R)-carbonyl)amino)phenylsulfanyl)-acetyl]mutilin is obtained and is treated with etheric hydrochloric acid at room temperature for ca. 1 hour. From the mixture obtained the solvent is removed under reduced pressure and the residue obtained is crystallized from ethyl acetate/hexane.

14-O-[(3-(Piperidine-2(R)-carbonyl)amino) phenylsulfanyl)acetyl]mutilin in the form of a hydrochloride is obtained.

EXAMPLE 2

14-O-[(2,6-Dimethyl-3-(piperidin-2(R)-carbonylamino)phenylsulfanyl)-acetyl]mutilin in the Form of a Hydrochloride A solution of 200 mg of 14-O-[(2,6-dimethyl-5-aminophenyl)sulfanyl-acetyl]mutilin in the form of a hydrochloride, 84 mg of N—BOC—(R)-pipecolic acid, 190.1 mg of PyBOP and 143 mg of DIEA in 20 ml of dioxane is kept for ca. 24 hours at ca. 40°. The mixture obtained is diluted with water and extracted with ethyl acetate. The organic phase is re-extracted with 0.1 N sodium hydroxide, 0.1 N hydrochloric acid and brine. The organic phase obtained is concentrated and the concentrate is subjected to chromatography (silica gel; toluene/ethyl acetate= 1.5/1). 14-O-[(2,6-Dimethyl-3(N—BOC—(R)-piperidin-2 (R)-carbonylamino)-phenylsulfanyl)-acetyl]mutilin is obtained. BOC is splitted off in a mixture of 10 ml of dioxane and 10 ml of etheric hydrochloric acid and 14-O-[(2,6-dimethyl-3(piperidin-2(R)-carbonylamino) phenylsulfanyl)-acetyl]mutilin in the form of a hydrochloride is obtained.

EXAMPLE 3

14-O-[(3-(Piperidine-2(R)-carbonyl)amino) phenylsulfanyl)-2(R*)-propionyl]mutilin in the Form of a Hydrochloride 206 mg of DCCl are added to a solution of 229 mg of N—BOC—(R)-pipecolic acid and 499 mg of 14-O-[(3-amino-phenylsulfanyl)-2-propionyl]mutilin in the form of a hydrochloride in 20 ml of dichloromethane at room temperature and the mixture obtained is stirred for ca. 12 hours at room temperature. Urea precipitates, is filtrated off and the filtrate obtained is concentrated under reduced pressure. The concentrate obtained is subjected to chromatography (silica gel; cyclohexane/ethyl acetate=1/1). 14-O-[(3-(N—BOC—(R)-piperidine-2(R)carbonyl)amino)phenylsulfanyl)-2(R*)-propionyl]mutilin is obtained and treated with etheric hydrochloric acid at room temperature for ca. 1 hour. From the mixture obtained the solvent is removed and the residue obtained is crystallized from ethyl acetate/hexane.

14-O-[(3-(Piperidine-2(R)-carbonyl)amino) phenylsulfanyl)-2(R*)-propionyl]mutilin in the form of a hydrochloride is obtained.

According to a method as described in examples 1 to 3, but using corresponding starting material, the compounds of formula I are obtained, wherein $R = R_3 = R'_3 = R_5 =$ hydrogen;

$R_4$ is methyl in examples 37 and 38, and hydrogen in all other examples;

$R_1$ is a group of formula —C(=X)$R_9$ in examples 1 to 35, 43 to 49 and hydrogen in examples 36 to 42;

X=O in examples 1 to 45, S in examples 46 and 47, N—CH$_3$ in example 48 and N$^+$(CH$_3$)$_2$ Cl in example 49;

$R_6 = R_7 = R_8$ in examples 1 to 11, 13 to 24, 26 to 28, 30, 32 to 39, 41 to 49 are hydrogen, and in examples 12, 25, 29, 31, 40 are deuterium;

and $R_2$ and $R_9$ are as defined in TABLE 1 below:

TABLE 1

| Example | R₉ | R₂ |
|---|---|---|
| 4 | 3-hydroxypyrrolidin-1-yl (trans, methyl substituted) | 1,4-dimethylphenyl |
| 5 | (S)-3-methylbutan-2-ylamino (isopropyl, CH(CH₃)₂ with NH₂) | 1,4-dimethylphenyl |
| 6 | 3-hydroxypyrrolidin-1-yl (trans, methyl substituted) | 1,3-dimethylphenyl |
| 7 | 2-methylpyrrolidin-1-yl | 1,3-dimethylphenyl |
| 8 | (S)-2-methylbutan-2-ylamino | 1,3-dimethylphenyl |
| 9 | (R)-3-methylbutan-2-ylamino | 1,2-dimethylphenyl |
| 10 | (S)-2-amino-1-propanol | 1,3-dimethylphenyl |
| 11 | 2-nitropyrrol-1-yl (NH, NO₂) | 1,3-dimethylphenyl |
| 12 | 2-methylpiperidinium (N⁺—D, D) Cl⁻ | 2,3-dimethyl-6-methylphenyl (trimethyl) |
| 13 | 3-methylpyridin-2-yl | 1,3-dimethylphenyl |

TABLE 1-continued
| Example | R9 | R2 |
|---|---|---|
| 14 | 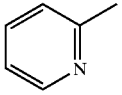 | 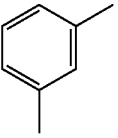 |
| 15 | 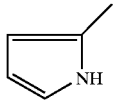 | 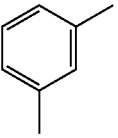 |
| 16 | 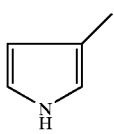 | 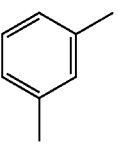 |
| 17 | 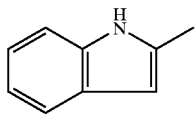 | 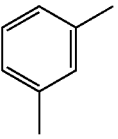 |
| 18 | 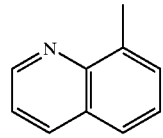 | 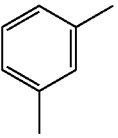 |
| 19 | 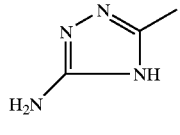 | 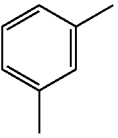 |
| 20 | 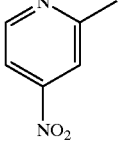 | 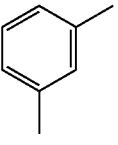 |
| 21 | 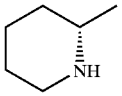 | 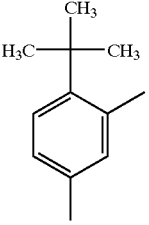 |
| 22 | 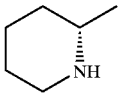 | 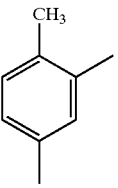 |

TABLE 1-continued
| Example | R<sub>9</sub> | R<sub>2</sub> |
|---------|---------------|---------------|
| 23 | H | 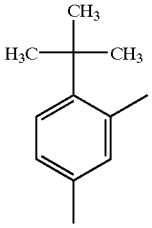 |
| 24 | H | 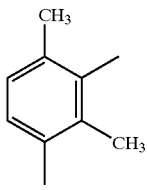 |
| 25 | 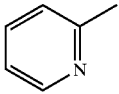 | 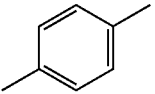 |
| 26 | 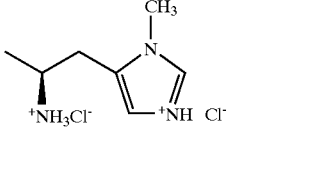 | 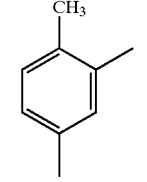 |
| 27 | 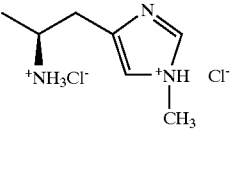 | 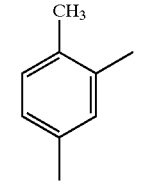 |
| 28 | 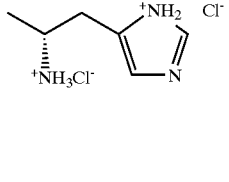 | 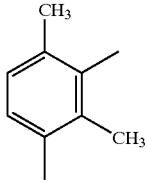 |
| 29 | 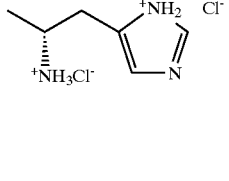 | 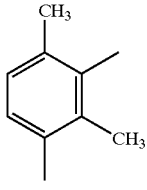 |
| 30 | 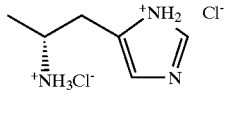 | 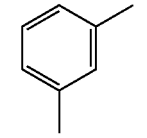 |

TABLE 1-continued

| Example | R₉ | R₂ |
|---|---|---|
| 31 | (S)-1-methyl-2-(1H-imidazol-5-yl)ethylammonium chloride, ⁺NH₃Cl⁻ | 3-methylphenyl |
| 32 | (S)-5-amino-N-(diaminomethylene)pentane-1-guanidinium, ⁺NH₃Cl⁻ ... ⁺NH₂ Cl⁻ | 2,4-dimethylphenyl |
| 33 | (S)-5-amino-N-(diaminomethylene)pentane-1-guanidinium, ⁺NH₃Cl⁻ ... ⁺NH₂ Cl⁻ | 2,3,4-trimethylphenyl |
| 34 | (S)-5-amino-N-(diaminomethylene)pentane-1-guanidinium, ⁺NH₃Cl⁻ ... ⁺NH₂ Cl⁻ | 3-methylphenyl |
| 35 | (S)-3-methylbutan-2-amine | together with N and R forms 3-methylpiperidine |
| 36 | — | 4-methylphenyl |
| 37 | — | 3-methylphenyl |
| 38 | — | 3-methylphenyl |
| 39 | — | 3-methylphenyl |

TABLE 1-continued

| Example | R₉ | R₂ |
|---|---|---|
| 40 | — | 3-methylphenyl |
| 41 | — | 2,3,5-trifluoro-6-methylphenyl (tetrasubstituted: F, F, CH₃, F with methyl attachment) |
| 42 | — | 2,5-dimethyl-nitrophenyl (dimethyl with NO₂) |
| 43 | CH₃ | 3-methylphenyl |
| 44 | CF₃ | 3-methylphenyl |
| 45 | H | 3-methylphenyl |
| 46 | H₃C—O—C(=O)—N— (ethyl carbamate, N-methyl) | 3-methylphenyl |
| 47 | H₃C—N(H)— | 3-methylphenyl |
| 48 | —S—CH₃ | 3-methylphenyl |
| 49 | H | 3-methylphenyl |

EXAMPLE 50

Replacement of Hydrogen Atoms by Deuterium Atoms in a Compound of Formula I

A solution of 300 mg of 14-O-[(3-(piperidine-2(R)-carbonyl)amino)phenylsulfanyl)acetyl]-mutilin-hydrochloride in 30 ml of dioxane and 5 ml of DCl (20% in $D_2O$) is kept for 6 days at room temperature, the mixture obtained is concentration under reduced pressure and lyophilixed to obtain 14-O-[(3-(piperidine-2(R)-carbonylamino)phenyl-sulfanyl)acetyl]-2,2,4-trideutero-mutilin in the form of a deuterochloride.

NMR(CDCl₃): In comparison to the NMR-Data of the compound of example 1 the signals of the 2-, 2'- and 4-protons of the tricyclic moiety are lacking.

According to the method as described in example 50 compound of formula I, wherein $R=R_3=R'_3=R_4=R_5=$ hydrogen; $R_1$ is a group of formula —(C=X)$R_9$, wherein X=O; $R_6=R_7=R_8$ are deuterium; and $R_2$ and $R_9$ are as defined in TABLE 2 below, in the form of a deuterochloride is obtained:

TABLE 2

| Example | $R_9$ | $R_2$ |
|---------|-------|-------|
| 51 | 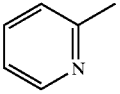 | 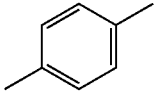 |

EXAMPLE 52

14-O-[(3-Amino-phenylsulfanyl)acetyl]mutilin

A solution of 0.92 g of sodium and 5 g of 3-aminothiophenol in 100 ml of dry ethanol is added to a solution of 21.3 g of 22-O-tosyl-pleuromutilin in 250 ml of ethylmethylketone at room temperature under temperature control. The reaction mixture obtained is kept for ca. 15 hours at room temperature, is filtered and is concentrated to dryness under reduced pressure. The residue is subjected to chromatography (silica gel; cyclohexane/ethyl acetate=1/1). 14-O-[(3-Amino-phenylsulfanyl)acetyl]mutilin is obtained.

Production of Starting Material
A. 14-O-[(3-Amino-phenylsulfanyl)acetyl]mutilin see Example 52
B. 14-O-[(2,6-Dimethyl-5-amino-phenyl)sulfanyl-acetyl]mutilin in the form of a hydrochloride
B.a 14-O-[(Carbamimidoylsulfanyl)acetyl]mutilin-tosylate A solution of 15.2 g of thiourea and 106.4 g of pleuromutilin-22-O-tosylate in 250 ml of acetone is heated under reflux for 1.5 hours, solvent is removed under reduced pressure and 100 ml of hexane is added. A precipitate forms, is filtrated off and dried. 14-O-[(Carbamimidoylsulfanyl)acetyl]mutilin-tosylate is obtained.

B.b 14-Mercapto-acetyl-mutilin

A solution of 4.7 g of sodium pyrosulfite ($Na_2S_2O_5$) in 25 ml of $H_2O$ is added to a solution of 12.2 g of 14-O-[(carbamimidoylsulfanyl)acetyl]mutilin-tosylate in a mixture of 20 ml of ethanol and 35 ml of $H_2O$ (warmed to ca. 90°). 100 ml of $CCl_4$ are added to the reaction mixture obtained and the mixture is heated under reflux for ca. 2 hours. The two-phase system obtained is separated, the organic phase is dried and the solvent is evaporated off. 14-Mercapto-acetyl-mutilin is obtained.

B.c 14-O-[(2,6-Dimethyl-5-nitrophenyl)sufanyl-acetyl]mutilin

A solution of 0.98 g of 2,4-dinitroxylene in 30 ml of HMPT is added to a solution of 3.94 g of 14-mercapto-acetyl-mutilin and 115 mg of sodium in 15 ml of methanol. The reaction mixture obtained is heated at to ca. 120° for ca. one hour, is kept for additional ca. 12 hours at room temperature and is poured onto ice. The mixture obtained is extracted with toluene the organic phase obtained is dried, and the solvent is evaporated off. The residue obtained is subjected to chromatograpy (silica gel (toluene/ethyl acetate=2/1). 14-O-[(2,6-Dimethyl-5-nitrophenyl)sulfanyl-acetyl]mutilin is obtained.

B.d 14-O-[(2,6-Dimethyl-5-amino-phenyl)sulfanyl-acetyl]mutilin in the form of a hydrochloride 2.5 g of tin powder are added to a solution of 202 mg of 14-O-[(2,6-dimethyl-5-nitrophenyl)sulfanyl-acetyl]mutilin in 10 ml of dioxane, 1.5 ml of formic acid and 0.1 ml of $H_2O$ and the reaction mixture obtained is heated for ca. 5 hours under reflux. The mixture obtained is filtrated and the solvent of the filtrate obtained is evaporated off. A mixture of 5 ml of dioxane and 10 ml of etheric hydrochloric acid is added to the residue obtained and the solvent of the mixture obtained is evaporated off. The residue is subjected to crystallization in ethyl acetate/hexane. Crystalline 14-O-[(2,6-dimethyl-5-amino-phenyl)sulfanyl-acetyl]mutilin in the form of a hydrochloride is obtained.

C. 14-O-[(3-Amino-phenylsulfanyl)-2-propionyl]mutilin in the form of a hydrochloride C.a 14-O-(2(R/S)-Bromo-propionyl)mutilin A solution of 3.2 g of mutilin, 2 g of N-methylmorpholine and 4.3 g of 2-bromo-propionylbromide in 50 ml of tetrahydrofuran is kept at room temperature for ca. 24 hours. The mixture obtained is concentrated under reduced pressure and the residue obtained is poured into a mixture of water and ethyl acetate. A two-phase system is obtained and the phases are separated. The organic phase obtained is extracted with 1 N HCl and brine and subjected to chromatography (cyclohexane/dioxane=6/1). 14-O-(2(R/S)-Bromo-propionyl)mutilin is obtained.

C.b 14-O-[(3-Amino-phenylsulfanyl)-2(R*)-propionyl]mutilin in the form of a hydrochloride; and 14-O-[(3-Amino-phenylsulfanyl)-2(S*)-propionyl]mutilin in the form of a hydrochloride A solution of 45 mg of 14-O-(2(R/S)-bromo-propionyl)mutilin, 125 mg of 3-amino-thiophenol and 24 mg of sodium in 10 ml of ethanol and 5 ml of ethylmethyl ketone is kept at room temperature for ca. 12 hours. Solvent of the mixture obtained is evaporated off and 50 ml of ethyl acetate are added to the residue obtained. The organic phase obtained is extracted with brine and subjected to chromatography (silica gel; cyclohexane/dioxane=6/1). A diastereoisomeric mixture of 14-O-[(3-Amino-phenylsulfanyl)-2(R/S)-propionyl]mutilin is obtained. The diastereoisomeres are separated by preparative HPLC-chromatography (cyclohexane/dioxane=8) and treated with hydrochloric acid. 14-O-[(3-Amino-phenylsulfanyl)-2(R*)-propionyl]mutilin in the form of a hydrochloride and 14-O-[(3-Amino-phenylsulfanyl)-2(S*)-propionyl]mutilin in the form of a hydrochloride are obtained.

¹H-NMR-Spectra (CDCl₃ if not otherwise specified)
Ex.
1 3.1, 3.5 (2×m, 2H, ϵ,ϵ'H-piperidine), AB-system ($v_A$=3.57, $v_B$=3.62, 2H, $H_{22}$, J=15.2 Hz), 4.42 (b, 1H, α-H-piperidine), 7.03 (d, 1H, arom.$H_6$, J=7.7 Hz), 7.13 (t, 1H, arom.$H_5$, J=5.9 Hz), 7.49 (d, 1H, arom.$H_4$, J=7.7 Hz), 7.85 (s, 1H, arom.$H_2$), 10.7 (s, 1H, NH).

2 2.48, 2.52 (2×s, 6H, 2×arom. CH$_3$), AB-system (v$_A$=3.3, v$_B$=3.38, 2H, H$_{22}$, J=15.8 Hz, 4.5 (b, 1H, α-H, piperidine), 3.1, 3.3 (2×b, 2H, ε, ε'-H, piperidine, 7.0, 7.4 (2×m, 2H, arom. H$_4$,H$_5$), 8.45, 9.6 (2×b, 2H, NH$_2$), 9.9 (b, 1H, NH).

3 (d$_6$-DMSO): 1.48 (d, 3H, C$_{22}$—CH$_3$, J=7.2 Hz), 2.75, 3.05 (2×b, 2H, ε,ε'-H-piperdine), 3.38 (d, 1H, H$_{11}$, J=6.35 Hz), 3.82 (q, 1H, H$_{22}$, J=7.2 Hz), 7.2 (t, 1H, arom.H$_5$, J=7.8 Hz), 7.15 (ddd, 1H, arom.H$_6$, J=7.8 Hz, J=1.5 Hz, J=2.8 Hz), 7.55 (ddd, 1H, arom.H$_4$, =7.8 Hz, J=1.5 Hz, J=2 Hz), 7.6 (t, 1H, arom.H$_2$, J=1.8 Hz), 8.9 (s, 1H, NH).

4 3,5 (s, 2H, H$_{22}$), 2.7, 3.4, 3.7, 4.6, (4×m, 5H, piperidine-H), 8.1, 9.7, 10.3 (3×b, 2×NH, OH), 7.45 (d, 2H, arom.H, J=6.2 Hz), 7.52 (d, 2H, arom.H, J=6.2 Hz).

5 1.08 (d, 6H, CH(Me)$_2$, J=6.2 Hz), AB-system (v$_A$=3.5, v$_B$=3.58, 2H, H$_{22}$, J=15.1 Hz), 3.92 (d, 1H, α-H, J=5.7 Hz), 7.7 (d, 2H, arom.H, J=6.2 Hz), 7.51 (d, 2H, arom.H, J=6.2 Hz).

6 3.5 (s, 2H, H$_{22}$), 2.7, 3.4, 3.7, 4.6, (4×m,5H, piperidine-H), 8.1, 9.7, 10.3 (3×b, 2×NH, OH), 7.01 (dd, 1H, arom.H$_6$, J=1.5 Hz, J=6.2 Hz), 7.18 (t, 1H, arom.H$_5$, J=6.2 Hz), 7.4 (dd, 1H, arom.H$_4$, J=1.5 Hz, J=6.2 Hz) 7.6 (d, NH, J=6 Hz).

7 3.6 (s, 2H, H$_{22}$), 5.01 (m, 1H, α-H), 7.1 (d, 1H, arom.H$_4$, J=8.2 Hz), 7.3 (t,1H, arom.H$_5$, J=8.2 Hz), 7.49 (d, 1H, arom.H$_6$, J=8.2 Hz), 7.82 (s,1H, arom.H$_2$), 7.6, 10.8 (2×b, 2×NH).

8 1.1 (d, 6H, (CH(Me)$_2$), J=6.5 Hz), AB-system (v$_A$=3.6, v$_B$=3.65, 2H, H$_{22}$, J=15.2 Hz), 3.92 (d, 1H, α-H, J=6.2 Hz), 7.12 (dd, 1H, arom.H$_6$, J=7.9 Hz, J=2.1 Hz), 7.25 (t, 1H, arom.H$_5$, J=7.9 Hz), 7.42 (dd, 1H, arom.H$_4$, J=7.9, J=2.1 Hz), 7.75 (d, 1H, arom.H$_2$, J=2.1 Hz).

9 1.08 (d, 6H, (CH(Me)$_2$), J=7 Hz), AB-system (v$_A$=3.42, v$_B$=3.5, 2H, H$_{22}$, J=15.2 Hz), 3.45 (d, 1H, α-H, J=4.1 Hz), 7.0, 7.35, (2×m, arom.H$_3$, H4), 7.51 (d, 1H, arom.H$_2$, J=7.5 Hz), 8.48 (d, 1H, arom.H$_6$, J=7.5 Hz), 10.55 (s, 1NH, NH).

10 AB-system (v$_A$=3.58, v$^B$=, 3.6, 2H, H$_{22}$, J=15.8 Hz), AB-system (v$_A$=3.58, v$_B$=3.59, CH2-OH, J=14.2 Hz), 3.67 (d,b, α-H, 4.9 Hz), 7.08 (dd, 1H, arom.H$_6$, J=7.9 Hz, J=2.1 Hz), 7.22 (t, 1H, arom.H$_5$, J=7.9 Hz), 7.45 (dd, 1H, arom.H$_4$, J=7.9, J=2.1 Hz), 7.65 (d, 1H, arom.H$_2$, J=2.1 Hz), 9.54 (b, 1H, NH).

11 3.62 (s, 2H, H$_{22}$), 6.75 (d, 1H, pyrrole-H, J=4.5 Hz), 7.12 (d, 1H, pyrrole-H, J=4.5 Hz), 7.18 (dd, 1H, arom.H$_6$, J=6.3 Hz, J=1.5 Hz), 7.28 (t, 1H, arom.H$_5$, J=6.3 Hz), 7.5 (dd, 1H, arom.H$_4$, J=6.3 Hz, J=1.5 Hz), 7.62 (d, 1H, arom.H$_2$, J=1.5 Hz), 7.95 (s, 1H, NH).

12 In comparison to the NMR-Data of example 2, the signals of the 2.2'-and 4-protons of the tricyclic moiety are lacking. MS m/e626(MH)$^+$.

13 3.65 (s, 2H, H$_{22}$), 7.3, 7.4, 7.8 (3×m, arom.H), 8.15 (s, 1H, arom.H2), 8.05, 8.8, 9.2, 10.4 (4×b, pyridine-H), 10.9 (b, 1H, NH).

14 3.65 (s, 2H, H$_{22}$), 7.18 (dd, 1H, arom.H$_4$, J=1 Hz, J=7.7 Hz,), 7.3 (t, 1H, arom.H$_5$, J=7.98 Hz), 7.73 (dd, 1H, arom.H$_6$, J=1 Hz, J=7.7 Hz), 8.03 (d, 1H, arom.H$_2$, J=2 Hz), 7.82, 8.3 (2×m, pyridine-H$_4$, H$_5$), 8.6 (d, 1H, pyridine-H$_6$, J=7.75 Hz), 8.73 (d, 1H, pyridine-H$_3$, J=4.5 Hz), 11.95 (s, 1H, NH).

15 3.6 (s, 2H, H$_{22}$), 7.10 (dd, 1H, arom.H$_4$, J=7.3 Hz, J=1.5 Hz), 7.24 (t, 1H, arom.H$_5$, J=8 Hz), 7.48 (dd, 1H, arom.H$_6$, J=7.3 Hz, J=1.5 Hz), 7.65 (d, 1H, arom.H$_2$, J=1.5 Hz), 6.3, 6.71, 7.0 (3×m, 3H, pyrrole-H), 7.62 (s, 1H, NH), 9.65 (s, 1H, NH).

16 AB-system (v$_{A=3.6}$, v$_B$=3.68, 2H, H$_{22}$, J=15.2 Hz), 6.52, 6.83, 7.48 (3×m, 3H, pyrrole-H), 7.08 (dd, 1H, arom.H$_4$, J=1.5 Hz, J=7.7 Hz), 7.23 (t, 1H, arom.H$_5$, J=7,9 Hz), 7.52 (dd, 1H, arom.H$_6$, J=1.5 Hz, J=7.7 Hz), 7.65 (d, 1H, arom.H$_2$, J=1.5 Hz), 7.42 (s, 1H, NH), 8.55 (b, 1H, NH).

17 3.62 (s, 2H, H$_{22}$), 7.15 (dd, 1H, arom.H$_6$, J=2 Hz, J=7.8 Hz), 7.34 (t, 1H, arom, H$_5$, J=8.2 Hz), 7.54 (dd, 1H, arom.H$_4$, J=2 Hz, J=7.8 Hz), 7.01, 7.18, 7.3, 7.45, 7.7 (5×m, indole-H), 7.88 (s, 1H, NH), 9.43 (s, 1H, NH).

18 AB-system (v$_A$=3.52, v$_B$=3.58, 2H, H$_{22}$, J=14.9 Hz), 6.8, 7.2, 7.4, 7.82, 7.9 (5×m, 6H, arom.H+quinoline-H), 7.83 (t, 1H, arom.H$_5$, J=7.7 Hz), 8.5 (d, 1H, chinoline-H$_1$), 8.75 (d, 1H, chinoline-H$_7$).

19 3.55 (sb, 2H, H$_{22}$), 7.03, 7.2, 7.55 (3×m, 3H, arom.H$_4$, H$_5$, H$_6$), 7.75 (s, 1H, arom.H$_2$), 7.7–8.1 (b, NH$_2$, NH), 9.6(b, 1H, NH).

20 3.65 (s, 2H, H$_{22}$), 7.15 (dd, 1H, arom.H$_6$, J=1.5 Hz, J=7.3 Hz), 7.32 (t, 1H, arom.H$_5$, J=7.9 Hz), 7.65 (dd, 1H, arom.H$_4$, J=1.5 Hz, J=7.7 Hz), 7.8 (d, 1H, arom.H$_2$, J=1.5 Hz), 8.22 (dd, 1H, pyridine-H$_5$, J=2.2 Hz, J=5.3 Hz), 8.95 (dd, 1H, pyridine-H$_6$, J=0.8 Hz, J=5.3 Hz), 8.99 (d, 1H, pyridine-H$_3$, J=2,2 Hz), 9.82 (s, 1H, NH).

21 1.45, (s, 9H, arom. tert.-butyl), AB-system (v$_A$=3.65, v$_B$=3.75, 2H, H$_{22}$, J=14.8 Hz), 4.4 (b, 1H, α-H, piperidine), 3.1, 3.5 (2×b, 2H, ε-H, piperidine), 7.18, 7.28 (2×m, 2H, arom.H$_4$, H$_3$), 7.7 (b, 1H, arom.H$_6$), 10.4 (b, 1H, NH).

22 2.48, (s, 3H, arom. CH$_3$), AB-system (v$_A$=3.2, v$_B$=3.36, 2H, H$_{22}$, J=15.8 Hz), 4.4 (b, 1H, α-H, piperidine), 3.1,3.5 (2×b, 2H, ε-H, piperidine), 7.0, 7.4 (2×m, 2H, arom.H$_4$, H$_3$), 7.8 (b, 1H, arom.H$_8$) 8.45, 9.6 (2×b, 2H, NH$_2$), 10.4 (b, 1H, NH).

23 Rotamere: 1.48 (s, 9H, tert.Butyl), AB-system (v$_A$=3.61 v$_B$=3.68, 1.2H, J=15 Hz, v$_A$=3.64, v$_B$=3.66, 0.8H, J=14.5 Hz), 7.1–7.5 (m, 2H, arom.H$_3$, H$_4$), 8.35 (d, 1H, arom.H$_6$, J=2 Hz), 8.65 (d, 0.8H, formyl-H, J=11 Hz, 8.67 (sb, 0.2H).

24 Rotamere: 2.5, 2.55 (2×s, 6H, arom.CH$_3$), AB-system (v$_A$=3.30, v$_{B=}$3.4, 1.2H, J=15 Hz, v$_A$=3.34, v$_B$=3.4, 0.8H, J=14.5 Hz), 7.05 (d, 0.5H, arom.H$_4$, J=8 Hz), 7.78 (d, 0.5H, arom.H$_4$, J=8 Hz), 7.1 (d, 1H, arom.H$_5$, J=8 Hz), 8.42 (d, 0.8H, formyl-H, J=11 Hz, 8.67 (sb, 0.2H), 6.9 (b, 1H, NH).

26 (in the form of a dihydrochloride) 7.52 (s, 1H,imidazole-H), 9.03 (s, 1H,imidazole-H), 8.65(b,2H,NH$_2$), 7.16(dd, 1H, arom.H$_6$, J=1.5 Hz, J=8.3 Hz), 7.42(dd, 1H, arom.H$_4$, J=1.5 Hz, J=8.3 Hz), 7.73(d, 1H, arom.H$_2$, J=1.5 Hz),11.4 (s,1H,NH), 4.45(m, 1H, α-H, amino acid), 3.8(s,3H,N—CH$_3$)AB-system (v$_A$=4.4, v$_B$=3.48, 2H, CH$_2$CH, J=15.2, 7.8 Hz, AB-system (v$_A$=3.75, v$_{B=}$3.65, 2H, H$_{22}$, J=15.2 Hz, 2.25(s,3H,arom.CH$_3$).

27 (in the form of a dihydrochloride) (d6-DMSO,350K): 11.8(s,1H,imidazole-H), 9.03(s,1H,imidazole-H), 8.65(b, 2H,NH$_2$), 7.16(dd, 1H, arom.H$_6$, J=1.5 Hz, J=8.3 Hz), 7.38(dd, 1H, arom.H$_4$, J=1.5 Hz, J=8.3 Hz), 7.73(d, 1H, arom.H$_2$, J=1.5 Hz), 7.54(s,1H,NH), 4.45(m,1H, α-H, amino acid), 3.3(s,3H,N—CH$_3$)AB-system (v$_A$=3.25, v$_B$=3.4, 2H, CH$_2$CH, J=15.2, 7.8 Hz, ABsystem (v$_A$=3.78, v$_B$=3.68, 2H, H$_{22}$, J=15.2 Hz, 2.25(s,3H,arom.CH$_3$).

28 (in the form of a dihydrochloride) 9.7(s,1H,NH),8.82(s, 1H),imidazole-H), 7.48(s,1H, imidazole-H), 8.45(b,3H, NH$_3$), 6.83(d, 1H, arom.H$_4$, J=8.4 Hz), 7.25(d, 1H, arom.H$_5$, J=8.4 Hz), 4.85(m,1H, α-H, amino acid), 3.38–3.5(m,2H, CH$_2$CH,amino acid), 2.3,2.38(2×CH$_3$, arom.CH$_3$), AB-system (v$_A$=3.08, v$_B$=3.18, 2H, H$_{22}$, J=15.2 Hz), MS m/e651 (MH)$^+$.

29 In comparison to the NMR-data of example 28, the signals of the 2.2'-and 4-protons of the tricyclic moiety are lacking. MS m/e684(MH)$^+$.

30 (in the form of a dihydrochloride) (d6-DMSO): 11.8(s, 1H,imidazole-H), 9.03(s,1H,imidazol-H), 8.6(b,2H, NH$_2$), 7.09(dd, 1H, arom.H$_6$, J=1.5 Hz, J=7.3 Hz), 7.27(t, 1H, arom.H$_5$, J=7.9 Hz), 7.43(dd, 1H, arom.H$_4$, J=1.5 Hz, J=7.3 Hz), 7.64(d,1H, arom.H$_2$, J=1.5 Hz),7.54(s,1H, NH), 4.43(m,1H, α-H, amino acid), 3.2–3.4(m,2H, CH$_2$CH,amino acid).

31 (in the form of a dideuterochloride). In comparison to the NMR-data of example 30 the signals of the 2.2'- and 4-protons of the tricyclic moiety are lacking. MS m/e625 (MH)$^+$.

32 (in the form of a hydrochloride) (d6-DMSO,): 7.52(s, 1H,imidazole-H), 9.03(s,1H, imidazole-H), 7.8(m,1H, NH$_2$),10.95(s,1H,NH), 8.45(s3H, NH$_3$) 7.16(dd, 1H, arom.H$_6$, J=1.5 Hz, J=8.3 Hz), 7.42(dd, 1H, arom.H$_4$, J=1.5 Hz, J=8.3 Hz), 7.73(d, 1H, arom.H$_2$, J=1.5 Hz), 4.05(m,1H, α-H, amino acid), 3.8(s,3H,N—CH$_3$),AB system (v$_A$=4.4, v$_B$=3.48, 2H, CH$_2$CH, J=15.2, 7.8 Hz, AB-system (v$_A$=3.78, v$_B$=3.68, 2H, H$_{22}$, J=15.2 Hz, 2.25 (s,3H,arom.CH$_3$).

33 (in the form of a hydrochloride) (d6-DMSO): 10.2(b,1H, NH), 8.5(b,3H,NH$_3$), 7.15(d, 1H, arom.H$_4$, J=8.2 Hz), 7.25(d, 1H, arom.H$_5$, J=8.2 Hz),4.13(t,1H,α-H, amino acid, J=6.6 Hz), 3.4(m,2H, δ-H,amino acid), AB-system (v$_A$=3.5, v$_B$=3.36, 2H, H$_{22}$, J=15.2 Hz), 2.41, 2.44(2×s, 6H,2×CH$_3$).

34 NMR (d6DMSO,350K): 10.9(b,1H,NH), 8.6(b, 4H,NH), 7.10(dd, 1H, arom.H$_6$, J=1.5 Hz, J=7.3 Hz), 7.27(t, 1H, arom.H$_5$, J=7.9 Hz), 7.50(dd, 1H, arom.H$_4$, J=1.5 Hz, J=3 Hz), 7.74(d, 1H, arom, H$_2$, J=1.5 Hz.), 4.13(t,1H, α-H, amino acid,J=6.6 Hz), 3.4(m, 2H, δ-H,amino acid), AB-system (v$_A$=3.6, v$_B$=3.68, 2H, H$_{22}$, J=15.2 Hz.

35 (in the form of a hydrochloride) (d6-DMSO,350K): 8.03(b,3H,NH$_3$), 4.25(d,1H, α-H, amino acid, J=4.6 Hz), AB-system (v$_A$=3.45, v$_B$=3.32, 2H, H$_{22}$, J=15.2 Hz 0.85, 0.95 (2×d, CH(CH$_3$)$_2$, J=5.9 Hz), 4.0(m,2H, NCH$_2$CH$_2$). MS m/e577(MH)$^+$.

36 7.26(d,2H,arom.H,J=8.6 Hz), 6.58(d,2H,arom.H,J=8.6 Hz) AB-system(v$_A$=3.42, v$_B$=3.38, 2H, H$_{22}$, J=14.4 Hz), Ms m/e: 621 (M$^+$+Na).

37 Compound (22-R*): (d$_6$-DMSO/CDCl$_3$1:3)):7.37(dd, 1H, arom.H$_6$, J=1.5 Hz, J=7.3 Hz), 7.27(t, 1H, arom.H$_5$, J=7.9 Hz), 7.34(dd, 1H, arom.H$_4$, J=1.5 Hz, J=7.3 Hz), 7.48(d, 1H, arom.H$_2$, J=1.5 Hz), 3.82(q,1H, CHCH$_3$,J=7.2 Hz), 1.49(d,3H,CHCH$_3$, J=7.2 Hz).

38 Compound (22-S*): (d$_6$DMSO/CDCl$_3$1:3)): 7.37(dd, 1H, arom.H$_6$, J=1.5 Hz, J=7.3 Hz), 7.27(t, 1H, arom.H$_5$, J=7.9 Hz), 7.34(dd, 1H, arom.H$_4$, J=1.5 Hz, J=7.3 Hz), 7.48(d, 1H, arom.H$_2$, J=1.5 Hz), 3.76(q,1H, CHCH$_3$,J=7.2 Hz), 1.52(d,3H,CHCH$_3$, J=7.2 Hz).

39 See data in example A below 40 in comparison to the NMR-data of compond 39 (in the form of an hydrochloride) the signals of the 2,2'- and 4-protons of the tricyclic moiety are lacking. MS m/e 489(M+1)$^+$.

41 7.45(m,1H,arom.H), AB-system(v$_A$=3.57, v$_B$=3.63, 2H, H$_{22}$, J=14.8 Hz).

42 6.88(dd,1H, arom.H$_6$, J=1.5 Hz, J=6.2 Hz), 7.32(dd, 1H, arom.H$_5$, J=1.5 Hz, J=6.2 Hz), 7.4(m,1H,arom.H$_3$) 3.59(s, 2H, H$_{22}$).

43 7.38(dd,1H, arom.H$_6$, J=1.5 Hz, J=6.2 Hz), 7.2 (t, 1H, arom.H$_5$, J=6.2 Hz), 7.05(dd, 1H, arom.H$_4$, J=1.5 Hz, J=6.2 Hz), 7.5(m,1H,arom.H$_2$), 3.4(s, 2H, H$_{22}$), 2.18(s, 3H,COCH$_3$).

44 7.9(b,1H,NH), 7.22(dd,1H, arom.H$_6$) J=1.5 Hz, J=6.2 Hz), 7.3(t, 1H, arom.H$_5$, J=6.2 Hz.), 7.43(dd, 1H, arom.H$_4$, J=1.5 Hz, J=62 Hz), 7.56(m,1H,arom.H$_2$), 3.62 (s, 2H, H$_{22}$).

45 7.48(s,1H,CH═O),6.80(dd,1H, arom.H$_6$, J=1.5 Hz, J=6.2 Hz), 7.14 (t, 1H, arom.H$_5$, J=6.2 Hz), 6.98(dd, 1H, arom.H$_4$, J=1.5Hz, J=6.2 Hz), 6.94(m,1H,arom.H$_2$), 3.58 (s, 2H H$_{22}$).

46 3.62(s, 2H, H$_{22}$), 7.23(dd,1H, arom.H$_6$, J=1.5 Hz, J=6.2 Hz), 7.3 (t, 1H, arom.H$_5$, J=6.2 Hz), 7.48(dd, 1H) arom.H$_4$, J=1.5 Hz, J=6.2 Hz), 7.75(m,1H,arom.H$_2$), 11.48, 8.05(2×b, NH), 4.3(q,2H,OCH$_2$CH$_3$, J=7.2 Hz), 1.38(t,3H, OCH$_2$CH$_3$, J=7.2 Hz).

47 7.72(s,1H,NH), 6.45(q,1H,NH,J=3.2 Hz), AB-system (v$_A$=3.52, v$_B$=3.6, 2H, H$_{22}$, J=14.8 Hz), 6.99(dd,1H, arom.H$_6$, J=1.5 Hz, J=6.2 Hz), 7.3 (t, 1H, arom.H$_5$, J=6.2 Hz), 7.3(m, 2H, arom.H$_4$, H$_2$), 3.28(d,3H,NCH$_3$,J=3.2 Hz).

48 7.72(s,1H,NH), 6.45(q, 1H, NH, J=3.2 Hz), AB-system (v$_A$=3.62, v$_B$=3.66, 2H, H$_{22}$, J=14.9 Hz), 7.75(m,1H, arom.H$_2$), 7.32(m,3H, arom.H$_6$, H$_5$,H$_4$), 3.18(b,3H, C═NCH$_3$)2.78(s,3H,SCH$_3$).

49 7.48(s,1H,NHCH═N)6.8(dd,1H, arom.H$_6$, J=1.5 Hz, J=6.2 Hz), 7.15 (t, 1H, arom.H$_5$, J=6.2 Hz), 6.99(dd, 1H, arom.H$_4$, J=1.5Hz, J=6.2 Hz), 6.95(m,1H,arom.H$_2$), 3.4 (s, 2H, H$_{22}$), 3.01 (s,6H,N(CH$_3$)$_2$).

A 0.58 (d, 3H, H$_{16}$, J=7.2 Hz), 0.81 (d, 3H, H$_{17}$, J=7.3 Hz), 1.02 (s, 3H, H$_{18}$), 1.32 (s, 3H, H$_{15}$), ABX-system (v$_A$=1.2, v$_B$=1.88, H$_{13a}$, H$_{13b}$, J=16.1 Hz, J=9.1 Hz), 2.08 (d,1H, H$_4$, J=2.1 Hz), ABXY-system (v$_A$=2.23, v$_B$=2.19, H$_{2a}$, H$_{2b}$, J=16.2 Hz, J=9.1 Hz, J=1.8 Hz), 2.3 (m, 1H, H$_{10}$), 3.4 (d,1H, H$_{11}$, J=5.98 Hz), AB-system (v$_A$=3.81, v$_B$=3.89, 2H, H$_{22}$, J=14.1 Hz), 5.18 (dd, 1H, H$_{20a}$,J=17.5 Hz, J=1.6 Hz), 5.29 (dd, 1H, H$_{20b}$, J=11 Hz, J=1.6 Hz), 5.51 (d, 1H, H$_{14}$, J=8.3 Hz), 6.05 (dd, 1H, H$_{19}$, J=11 Hz, J=17.5 Hz), 7.0 (m, 1H arom.H), 7.18 (m, 2H) arom.H), 7.3 (t,1H, arom.H$_5$, J=8 Hz).

B.a AB-system (v$_A$=3.7, v$_B$=3.82, 2H, H$_{22}$, J=15.8 Hz), 7.2 (d, 2H, arom.H, J=8Hz), 7.75 (d, 2H, arom.H, J=8 Hz), 8.4, 9.8 (2×b, 4H, 2×NH$_2$).

B.b ABX-system (v$_A$=3.15, v$_B$=3.22, v$_x$=1.92, 2H, H$_{22}$, J=15.8 Hz, J=8.2 Hz).

B.c 2.43, 2.48 (2×s, 6H, 2×arom. CH$_3$), AB-system (v$_A$=3.22, v$_B$=3.4, 2H, H$_{22}$, J=13.8 Hz), 6.7, 6.95 (2×d, 2H, arom.H$_4$,H$_5$).

B.d 2.61, 2.74 (2×s, 6H, 2×arom. CH$_3$), AB-system (v$_A$=3.31, v$_B$=3.43, 2H, H$_{22}$, J=15.8 Hz), 7.2, 7.7 (2×d, 2H, arom.H$_4$, H$_5$).

C.b (R) (d$_6$-DMSO):1.35 (d, 3H, C$_{22}$—CH$_3$, J=7.2 Hz), 3.25 (d, 1H, H$_{11}$, J=6.35 Hz), 3.75 (q, 1H, H$_{22}$, J=7.2 Hz), 7.18 (t, 1H, arom.H$_5$, J=7.8 Hz), 7.24 (ddd, 1H, arom.H$_6$, J=7.8 Hz, J=1.5 Hz, J=2.8 Hz), 7.28 (ddd, 1H, arom.H$_4$, =7.8 Hz, J=1.5 Hz, J=2 Hz), 7.43 (t, 1H, arom.H$_2$, J=1.8 Hz).

C.b (S) (d$_6$-DMSO):1.48 (d, 3H, C$_{22}$—CH$_3$, J=7.2 Hz), 2.4–3.2 (b, 2H, NH$_2$) 3.38 (d, 1H, H$_{11}$,=6.35 Hz), 3.82 (q, 1H, H$_{22}$, J=7.2 Hz), 7.28 (t, 1H, arom.H$_5$, J=7.8 Hz), 7.34(ddd, 1H, arom.H$_6$, J=7.8 Hz, J=1.5 Hz, J=2.8 Hz), 7.36 (ddd, 1H, arom.H$_4$, =7.8 Hz, J=1.5 Hz, J=2 Hz), 7.49 (t, 1H, arom.H$_2$, J=1.8 Hz).

What is claimed is:

1. A compound of formula

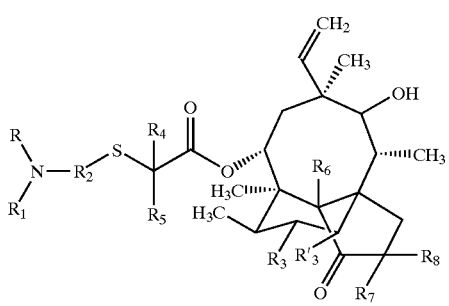

wherein
R and $R_2$ together with the nitrogen atom to which they are attached form non-aromatic heterocyclene;
$R_1$ is a group of the formula

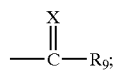

$R_3$, $R_3'$, $R_6$, $R_7$, and $R_8$ are independently of each other hydrogen or deuterium;
$R_4$ is hydrogen or alkyl;
$R_5$ is hydrogen or alkyl;
$R_9$ is amino, alkyl, aryl, heterocyclyl, or mercapto; and, if X is oxygen, $R_9$ is additionally hydrogen;
$R_{10}$ is hydrogen or alkyl; and
X is sulphur, oxygen, $NR_{10}$, or $N^{+(R'}_{10})_2$ wherein $R'_{10}$ is alkyl in the presence of an appropriate anion.

2. A compound of claim 1, wherein
$R_4$ is or alkyl;
$R_5$ is hydrogen;
$R_3$ and $R_3'$ are hydrogen;
$R_9$ is alkyl; and
X is oxygen.

3. A compound of the formula

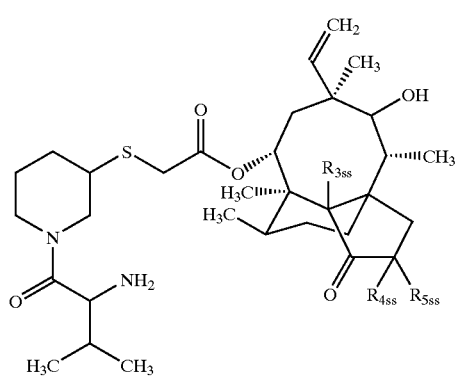

wherein $R_{3ss}$, $R_{4ss}$, and $R_{5ss}$ are hydrogen or deuterium.

4. A compound which is
14-O-(1-(2-amino-isobutylcarbonyl)-piperidin-3-yl-sulfanylacetyl)mutilin; or
14-O-(1-(2-amino-isobutylcarbonyl)-piperidin-3-yl-sulfanylacetyl)-2,2,4-trideutero-mutilin.

5. A compound of claim 1 in the form of a salt, or in the form of a salt and in the form of a solvate, or in the form of a solvate.

6. A process for the production of a compound claim 1, comprising the steps either a1. either reacting a compound of formula

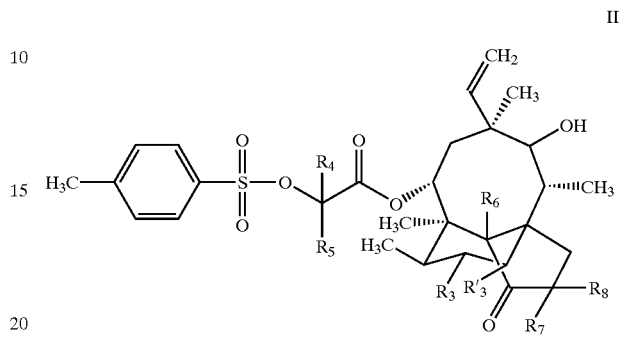

wherein $R_6$, $R_7$, and $R_8$ are hydrogen, with a compound of the formula $N(R)(R_1)$—$R_2$—SH to obtain a compound of formula I, wherein $R_6$, $R_7$, and $R_8$ are hydrogen; and, if desired, b1. introducing deuterium into said compound obtained in step a1 to obtain a compound of formula I, wherein $R_6$, $R_7$, and $R_8$ are deuterium;

or a2. reacting a compound of formula II with thiourea and subsequently reducing the product of said reaction to obtain a compound of the formula

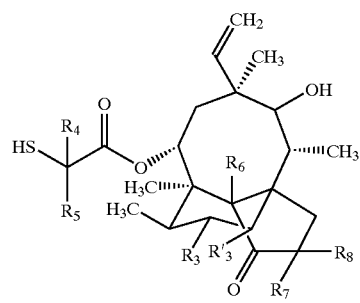

wherein $R_6$, $R_7$, and $R_8$ are hydrogen;

b2. reacting said compound of formula III with a non-aromatic heterocyclic ring which carries a group of formula —C(=X)$R_9$ in the form of a reactive derivative; and c. introducing deuterium into a compound obtained in step b2, to obtain a compound of formula I, wherein $R_6$, $R_7$, and $R_8$ are deuterium.

7. A method of treatment of microbial diseases comprising administering to a subject in need of such treatment an effective amoount of a compound of claim 1.

8. A pharmaceutical composition comprising a compound of claim 1, in free form or in the form of a pharmaceutically acceptable salt in association with at least one pharmaceutical carrier or diluent.